United States Patent
Lemonds et al.

(10) Patent No.: US 7,820,854 B2
(45) Date of Patent: Oct. 26, 2010

(54) PROCESS FOR CONVERTING ALKANES TO UNSATURATED CARBOXYLIC ACIDS

(75) Inventors: Andrew Michael Lemonds, Schwenksville, PA (US); Eric Gustave Lundquist, North Wales, PA (US); Donald Lee Zolotorofe, Ivyland, PA (US)

(73) Assignee: Rohm and Haas Company, Philadelphia, PA (US)

( * ) Notice: Subject to any disclaimer, the term of this patent is extended or adjusted under 35 U.S.C. 154(b) by 0 days.

(21) Appl. No.: 12/077,383

(22) Filed: Mar. 19, 2008

(65) Prior Publication Data

US 2009/0240081 A1    Sep. 24, 2009

(51) Int. Cl.
*C07C 27/10*    (2006.01)
*C07C 51/21*    (2006.01)
*C07C 45/27*    (2006.01)

(52) U.S. Cl. .................... 562/512.2; 562/549; 562/547; 562/546; 568/401; 568/469

(58) Field of Classification Search ........................ None
See application file for complete search history.

(56) References Cited

U.S. PATENT DOCUMENTS

| | | | |
|---|---|---|---|
| 3,948,959 | A | 4/1976 | Cavaterra et al. |
| 5,198,580 | A * | 3/1993 | Bartek et al. ................. 562/542 |
| 6,646,158 | B1 * | 11/2003 | Karim et al. ............. 562/512.2 |
| 2003/0181762 | A1 | 9/2003 | Machhammer et al. |
| 2004/0082190 | A1 | 4/2004 | Borgmeier et al. |
| 2005/0272952 | A1 | 12/2005 | Cremer et al. |
| 2007/0161812 | A1 * | 7/2007 | Lemonds et al. ............ 558/321 |

FOREIGN PATENT DOCUMENTS

| | | |
|---|---|---|
| EP | 1 815 907 A | 8/2007 |
| WO | WO 00/29106 A | 5/2000 |

\* cited by examiner

*Primary Examiner*—Porfirio Nazario Gonzalez
*Assistant Examiner*—Yate' K Cutliff
(74) *Attorney, Agent, or Firm*—Tifani M. Cottingham

(57) ABSTRACT

The present invention relates to an improved process for the conversion of alkanes to unsaturated carboxylic acids.

6 Claims, No Drawings

PROCESS FOR CONVERTING ALKANES TO UNSATURATED CARBOXYLIC ACIDS

The present invention relates to an improved process for the selective partial oxidation of alkanes to unsaturated carboxylic acids whereby the concentration of byproduct saturated carboxylic acids contained in the final oxidation product is lowered as compared to that derived from the traditional alkane partial oxidation process.

As used herein, the use of the term "(meth)acrylate" refers to both acrylates and methacrylates. Similarly, the term "(meth)acrylic" refers to either acrylic or methacrylic; the term "(meth)acrylic acid" refers to either acrylic acid or methacrylic acid.

Acrylic acid (AA), one example of an unsaturated carboxylic acid, is used in a wide variety of applications. Typical end-use applications include: acrylic plastic sheeting; molding resins; polyvinyl chloride modifiers; processing aids; acrylic lacquers; floor polishes; sealants; auto transmission fluids; crankcase oil modifiers; automotive coatings; ion exchange resins; cement modifiers; water treatment polymers; electronic adhesives; metal coatings; and acrylic fibers. AA is especially prized in these applications and others because of the hardness it imparts to the products in which it is used. It also enhances chemical stability and light stability, as well as ultraviolet radiation resistance, when used in certain products. Therefore, AA is often used in applications requiring resins of excellent transparency, strength, and outdoor durability. The AA market is extremely cost-sensitive; thus, any improvement in process yield, however slight, can result in significant cost-savings.

Propionic acid (PA), present as an impurity in AA produced by the selective partial oxidation of propane is an undesirable volatile organic compound. Current commercial AA processes employing a two-step partial oxidation of propene yield PA concentrations of less than 1,000 ppm, which is a typical specification level. AA made by the partial oxidation of propane, on the other hand, may contain between 3,000 and 30,000 ppm PA by weight due to the inherent higher selectivity of PA on propane versus the two-step partial oxidation of propene. These concentrations of PA pose significant product quality problems for AA made by propane oxidation, especially since AA and PA cannot be separated by conventional distillation due to their nearly identical boiling points. Furthermore, the extraction of PA from AA using common solvents, such as isopropyl acetate, toluene or diphenyl ether, is also unsuccessful due to similarity in solubility. As propane oxidation is becoming an economically attractive route to AA, new techniques for PA removal are needed to achieve increased purity levels of AA.

One attempt to increase AA purity is found in US Published Patent Application 2005/0272952. Although the reference recognizes the importance of a high purity product in general, it fails to distinguish between the byproducts formed during reaction. Because of a lack of selectivity, US 2005/0272952 lowers the sum of all byproducts and discloses a method for the partial combustion of those byproducts. This is unfavorable because certain byproducts, such as acetic acid, have value and may be recovered in downstream separations.

The present invention solves these problems associated with obtaining high purity unsaturated carboxylic acids, especially in propane-derived AA by adjusting process conditions and conducting selective chemical reactions to convert PA within AA process streams to other compounds such as AA itself or those which may be more easily separated or tolerated as impurities. This problem similarly exists for higher carbon analogues, e.g., isobutyric acid impurity present in methacrylic acid obtained by the selective partial oxidation of isobutane, and the present invention seeks to solve the problem of eliminating saturated carboxylic acids from unsaturated carboxylic acids, especially where the two acids have the same number of carbon atoms and similar boiling points. Useful chemistries, listed in Table 1 and described further below, include oxidative dehydrogenation (ODH) and aldol condensation reactions.

Table 1 also captures the main reaction products when PA is the substrate.

TABLE 1

Potential chemistries for saturated carboxylic acid removal

| Reaction | Main PA products |
| --- | --- |
| Oxidative dehydrogenation | acrylic acid |
| Aldol condensation | methacrylic acid |

The present invention is a method for lowering the concentration of saturated carboxylic acids present in a mixture of saturated and unsaturated carboxylic acids derived from the partial oxidation of C3 to C8 alkanes in a process comprising:
i) reacting the alkane with oxygen or an oxygen-containing gas, such as air, in the presence of a partial oxidation catalyst to yield a product comprising at least one unsaturated carboxylic acid and a concentration of the saturated carboxylic acid and
ii) lowering the impurity concentration of the saturated carboxylic acid by lowering the partial oxidation reaction selectivity to the saturated carboxylic acid or destroying, converting, or separating at least a portion of the saturated carboxylic acid.

According to the present invention, the efficacy of the chemical reaction process may be characterized in terms of the "feed conversion" and the "product yield." More particularly, feed conversion, or simply "conversion," is the percentage of the total moles of feed (e.g., $C_3$ to $C_8$ alkanes, such as propane and isobutane, or a mixture thereof) that have been consumed by the reaction. The product yield, or simply "yield", is the percentage of the theoretical total moles of the desired unsaturated carboxylic acid product, for example acrylic or methacrylic acid, that would have been formed if all of the feed had been converted to that product as opposed to unwanted side products. For example, in the case of propane oxidation, unwanted side products include acetic acid, CO, and $CO_2$. The aforesaid terms are generally defined as follows:

$$\text{feed conversion } (\%) = 100 \times \left( \frac{\text{moles of feed converted}}{\text{moles of feed}} \right)$$

$$\text{product yield } (\%) = 100 \times \left( \frac{\text{moles of product produced}}{\text{moles of feed}} \right)$$

In one aspect of the present invention, the method comprises reacting in a single reaction vessel at least one $C_3$-$C_8$ straight chain or branched alkane. As used herein, the term "$C_3$-$C_8$ straight chain or branched alkane" means a straight chain or branched chain alkane having from 3 to 8 carbons atoms per alkane molecule, for example, propane, butane and pentane. Particularly, $C_3$-$C_5$ straight chained or branched alkanes are examples of alkanes of the present invention.

According to the present invention, the alkane comprises propane and the unsaturated carboxylic acid comprises acrylic acid. The alkane is reacted with oxygen or oxygen present in a mixture with an inert gas, such as nitrogen, in the presence of a catalyst at a temperature ranging from upper limits of 550° C., 480° C., and 400° C. to lower limits of 250° C., 275° C., and 300° C. All temperature ranges are inclusive and combinable.

In one embodiment, the catalyst comprises a mixed metal oxide (MMO) having the empirical formula $$A_a M_b N_c X_d Z_e O_f$$

wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when a=1, b=0.01 to 1.0, c=0.01 to 1.0, d=0.01 to 1.0, e=0 to 0.1, and f is dependent on the oxidation state of the other elements.

According to the present invention, the reactants are admixed or otherwise provided with a diluent. The diluent is preferably a gas at room temperature and ambient pressure; and is inert to the reaction environment under the existing reaction conditions. Suitable gases include nitrogen, argon, helium and the like. The amount of diluent is not particularly important, however, it is preferably present in an amount of from greater than 0.1 mole percent to less than 70 mole percent, based on the total feed to the reactor, when used. Also, steam may be present in the feed gas in an amount varying from zero to 50 percent.

According to the present invention, suitable reaction vessels are designed to conduct vapor-phase, heterogeneous reactions and include but are not limited to fixed bed, fluidized bed, plate and frame, and micro-channel reactors. Where propane is used as the starting alkane and air is used as the oxygen source, the reaction vessel may be a fixed bed system or a fluidized bed system. However, since the reaction is an exothermic reaction, a fluidized bed system may preferably be employed whereby it is easy to control the reaction temperature. The proportion of air to be supplied to the reaction system is important for the selectivity for the resulting acrylic acid, and it is usually at most 25 moles, but usually ranges from 0.2 to 18 moles per mole of propane, whereby high selectivity for acrylic acid can be obtained. This reaction can be conducted under atmospheric pressure. However, the reaction may also be conducted under a slightly elevated pressure or slightly reduced pressure. With respect to other alkanes, for example isobutane, the composition of the feed gas may be selected in accordance with the conditions for propane.

Typical reaction conditions for the oxidation of propane to acrylic acid or methacrylic acid may be utilized in the practice of the present invention. The process may be practiced in a single pass mode where only fresh feed is fed to the reactor, or in a recycle mode where at least a portion of the reactor effluent is returned to the reactor. General conditions for the process of the present invention are as follows: the reaction temperature varies ranges from upper limits of 550° C., 480° C., 400° C. to lower limits of 250° C., 275° C., and 300° C.: to the gas space velocity, "SV", in the vapor phase reactor is typically within a range from upper limits of 10,000, 6,000, and 2,000 hr−1 to lower limits of 300, 200, and 100 hr−1; the average contact time with the catalyst can range from upper limits of 10, 8, 6, and 2 seconds to lower limits of 0.01, 0.01, 0.5, and 1 seconds; and the pressure in the reaction zone usually ranges from 0 to 75 psig, but is typically no more than 50 psig. All of the aforementioned range values are inclusive and combinable within a given set. In a single pass mode process, it is preferred that the oxygen be supplied from an oxygen-containing gas such as air. The single pass mode process may also be practiced with oxygen addition. In the practice of the recycle mode process, oxygen gas by itself is the preferred source so as to avoid the build up of inert gases in the reaction zone.

Surprisingly, it has been discovered that catalyst bed temperatures of greater than about 370° C. contribute to a significant lowering of propionic acid concentration. In some cases, especially for highly active propane oxidation catalysts that achieve high conversion at relatively low temperatures, it may therefore be necessary to increase the catalyst bed temperature. In order to do so for a given degree of propane conversion, the catalyst weight-based residence time must be decreased, thereby requiring higher temperatures to reach maximum yield. This condition may be achieved by increasing the feed rate for the same amount of catalyst or decreasing the amount of catalyst for the same feed rate. The displaced catalyst would be replaced by inert diluent in the reactor. If the residence time is lowered by increasing feed rate, increased throughput is also achieved. Additionally, lower propane to oxygen ratios in the feed gas was found to decrease the PA concentration. For example, lowering the propane-to-oxygen ratio from 0.71 (for a 7.1% propane, 10.0% oxygen, 23.0% water, and 59.9% nitrogen feed) to 0.20 (for a 3.0% propane, 14.7% oxygen, 23.0% water, and 59.3% nitrogen feed) decreased the PA concentration from 18,500 ppm to 10,700 ppm. These process adjustments of increasing reaction temperature and decreasing the propane-to-oxygen ratio can be performed individually or in combination with each other.

As a result of reacting at least one alkane with oxygen or an oxygen-containing gas, such as air, in the presence of at least one catalyst, a product is formed that comprises a least one unsaturated carboxylic acid and a concentration of a saturated carboxylic acid. At least a portion of the concentration of saturated carboxylic acid is then converted or separated. As used herein, "converted" means that the saturated carboxylic acid reacts with the exception of combustion, with another active agent to form a byproduct that is something other than the saturated carboxylic acid. As used herein, "removal chemistry" refers to the chemistry employed in the conversion of the saturated carboxylic acid. As used herein, "separated" means that the saturated carboxylic acid itself is disassociated from the unsaturated carboxylic acid in such a way as it may be removed from the system.

For the implementation of converting PA, two primary process solutions are conceivable. A co-catalyst may be placed within the alkane oxidation reactor ("co-catalyst" option) for in-situ removal of the saturated carboxylic acid, or a separate, downstream finishing reactor ("finishing reactor" option) may be incorporated as a possible choice for integrating the removal chemistry into AA manufacturing processes.

In the case of the co-catalyst option, the co-catalyst may be included within the alkane oxidation reactor's normal catalyst bed, for example, within the catalyst-packed tubes of a shell-and-tube reactor or other available reaction volume within the reactor, for example, within the headspace between the tube sheet and reactor outlet to remove the saturated carboxylic acid. The catalyst may be present neat or diluted with an inert material and partitioned from or mixed with the alkane oxidation catalyst. The co-catalyst and its associated chemistry must be compatible with the alkane oxidation process and process stream, and thus, it must also proceed in the same phase as the alkane oxidation process; if the oxidation is conducted in the vapor phase, so must be the catalytic saturated carboxylic acid removal process.

Suitable co-catalysts for conducting ODH reactions include, but are not limited to: iron phosphate and promoted iron phosphate catalysts as described in U.S. Pat. No. 3,948,959; and unsupported or supported oxides of at least one metal selected from the group comprising Mo, P, Fe, and V or combinations thereof. Additionally, the catalyst may be a reducible metal oxide promoted with a Group 8 metal. Thus, the catalyst may be a binary, ternary, quaternary or higher order compound. The reducible metal oxide may be an oxide of a metal selected from the group consisting of Cu, Cr, V, Mn, Nb, Mo, W, Re, Ga, Ge, In, Sn, Sb, Tl, Pb, Bi, Te, As, Se, Zn, Y, Zr, Ta, Ce, Pr, Nd, Pm, Sm, Eu, Gd, Tb, Dy, Ho, Er, Tm, Yb, Lu and mixtures thereof. Preferably, the reducible metal oxide is selected from the group consisting of Cu, Cr, V, Mn, Zn and mixtures thereof. The promoter is a metal from Group 8 of the Periodic Table of the Elements (Fe, Ru, Os, Co, Rh, Ir, Ni, Pd and Pt), preferably a metal selected from the group consisting of Pt, Pd, Rh, Ir, Ru and mixtures thereof. The promoter may preferably be present in amount ranging from upper limits of 10, 5, and 2 wt % to lower limits of 0.0001, 0.001, and 0.01 wt % of the catalyst composition which includes promoter and reducible metal oxide. All ranges are inclusive and combinable.

In the case of the finishing reactor option, a separate, downstream finishing reactor is included into the AA manufacturing process. This option offers greater flexibility in that said reactor may be inserted into the process at a number of points downstream from the alkane oxidation reaction as desired or best suited for the selected removal chemistry. For example, crude or purified AA, rather than the alkane oxidation product gas, may be subjected to the finishing reactor. Also, the removal chemistry in this case does not need to be directly compatible with the alkane oxidation process stream, as the saturated carboxylic acid removal is conducted ex-situ to the alkane oxidation reaction. If oxygen, for example, is detrimental to the selected removal chemistry, it may be separated prior to the finishing reactor. Furthermore, the chemistry implemented in the finishing reactor may be in a phase other than the alkane oxidation reaction phase.

In one embodiment, the ODH of propionic acid to acrylic acid as described in U.S. Pat. No. 3,948,959 offers an inherently selective pathway for PA removal because AA is the main product of the reaction; this technique, in theory, allows the PA to be removed without converting the desired product AA. However, the over-oxidation of AA (e.g., to acetic acid, CO and $CO_2$) by the ODH catalyst is a parasitic reaction that can destroy AA. The propane oxidation and PA ODH processes have in-situ compatibility because both systems are conducted in the vapor phase, require oxygen as the feed, and have the same main reaction product, AA. Thus, the alkane oxidation product stream, on the basis of the effluent acids, resembles that of an ODH product stream for which the saturated acid is the feed. At high conversion, i.e., for substantial or complete conversion of the feed, the product acid streams of these two processes are the same. For example, propane oxidation primarily yields AA, and propionic acid ODH also primarily yields AA. Our studies have shown ODH catalysts, such as $FePO_4$, to be active and selective for propionic acid ODH and, surprisingly, to be inactive under the process conditions investigated for AA over-oxidation. ODH is therefore an excellent choice for the co-catalyst option.

In another embodiment, aldol condensation reactions are used in a finishing reactor to selectively react the saturated carboxylic acids with an aldehyde co-reactant in the presence of a basic catalyst to yield unsaturated adducts of the saturated carboxylic acid. Aldol condensation reactions as taught in the patent literature and as practiced commercially (methyl propionate condensation with formaldehyde to produce methyl methacrylate by Lucite's Alpha process), are not conducted in the presence of oxygen, hence this reaction must be conducted ex-situ to alkane oxidation reaction and in a finishing reactor. Aldol condensations enable C—C bond formation, which result in adducts having a higher molecular weight of the acid. Thus, these higher molecular weight species can be more easily separated from the unsaturated carboxylic acid. Also, aldehyde precursors may be fed to the aldol condensation in place of an aldehyde. Suitable formaldehyde precursors, for example, include, but are not limited to, aqueous methylal and hexamethylene tetraamine. Suitable basic catalysts for the aldol condensation reaction include, but are not limited to: silica-supported oxides of Cs, Nb, and Sb; silica-supported $SnCl_2$; and aluminosilicates.

In one means of carrying out the above embodiment for the removal of PA from AA, the PA impurity is reacted with formaldehyde to form methacrylic acid. This means has an additional benefit in that acetic acid, another impurity produced by the oxidation of propane and, undergoes aldol condensation with formaldehyde to form AA. Thus, a crude AA stream comprising AA, PA, and acetic acid could be subjected to the aldol condensation process and the typical distillation of the crude AA to remove the acetic acid could be avoided.

In another aspect of the invention, the PA is separated from the AA by an adsorptive distillation process in which olefin-metal ion complexation is used to increase the relative volatility of PA in AA. For all practical purposes, in normal industrial acrylic acid purification columns, acrylic acid and propionic acid co-distill; although co-distillation is not a necessity. In the present invention, a packed distillation column having an active packing that retards the movement of acrylic acid (an oxygenate containing an olefinic moiety) up the column enhances the separation of propionic acid (NBP=141.1° C.; overhead cut) from acrylic acid (NBP=141.6° C.; bottoms cut). Adsorptive distillation processes using stationary, active packing to affect difficult separations, such as breaking azeotropes, are well known to those of ordinary skill in the art. Active packing suitable for the present invention include those that exhibit selective, reversible interactions with acrylic acid. It is well known that certain transition metals, especially silver, form complexes with olefins, and this behavior has been used to separate fatty acids with varying degrees of unsaturation using chromatographic methods. Similarly, olefin complexation has been used in absorptive processes, such as the use of silver and copper ions for the selective absorption of ethylene from an ethane-ethylene mixture. Surprisingly however, it has been discovered that a distillation column packed with a high-surface area active packing containing, or having distributed on its surface, a metal that forms olefin complexes can be used to separate propionic acid from a stream comprising acrylic and propionic acids. Such metals include but are not limited to transition metals of the Periodic Chart of Elements having atomic numbers above 20. Included in these metals are those of the first transition series having atomic numbers from 21 to 29, such as chromium, copper, especially the cuprous ion, manganese and the iron group metals, e.g., nickel and iron. Others of the useful complex-forming metals are in the second and third transition series, i.e. having atomic numbers from 39 to 47 or 57 to 79, as well as mercury, particularly as the mercuric ion. Thus, one may employ noble metals such as silver, gold and the platinum group, among which are platinum, palladium, rhodium, ruthenium and osmium. The useful base metals of the second and third transition series include, for example, molybdenum, tungsten and rhenium. Various combinations of these complex-forming metals may also be employed in this invention, either in the presence or absence of other non-metal or non-complexing metal cations.

In another aspect of the invention, the PA is separated from the AA by an extractive distillation process in which a Lewis base is complexed with the acids. AA (pKa=4.26) is more acidic than PA (pKa=4.88), and the Lewis base will therefore preferentially complex with the AA. When a Lewis base, such as dimethyl sulfoxide, dimethyl formamide, sulfolane, butyrolactone, or dimethylacetamide, is co-fed to a distillation column to with a feed comprising AA and PA, more acid-base complex is formed with the AA, and the volatility of the AA is reduced compared to the PA. AA may then be separated from the PA, thereby increasing the AA purity.

EXAMPLES

Comparative Example 1

A bulk powder mixed metal oxide (MMO) catalyst having a $MoV_{0.285}Te_{0.21}Nb_{0.17}Pd_{0.01}$ oxide bulk composition (as measured by X-ray fluorescence) was synthesized and pressed to particles of 14 to 20 mesh particle size. A 4 cm long catalyst bed comprising 4.43 g of the MMO catalyst mixed with 4 cc of inert carborundum packing was loaded and centered into a 1.27 cm diameter and 1.16 m long stainless steel plug flow tubular reactor. The remaining volume of the reactor tube was loaded with inert carborundum packing.

The reactor was heated by an annular electric furnace into which the reactor tube was installed, centered about the catalyst bed. The internal diameter and length of the furnace were 4.128 cm and 30.48 cm, respectively. The furnace temperature was measured by a thermocouple mounted in the annular space between the reactor tube and inner surface of the furnace. A movable thermocouple was also installed in a thermowell within the reactor tube for measurement of the bed temperature.

A vapor feed comprising 7.0% propane, 70.0% air, and 23% water was fed to the reactor at a total flow rate of 80 standard cubic centimeters per minute. Analyses of the condensable effluents (e.g., acrylic acid, acetic acid, and propionic acid) and the non-condensable effluents (oxygen, nitrogen, and carbon oxides) were conducted by gas chromatography methods known to those skilled in the art.

The reaction was conducted at furnace temperatures ranging from 300 to 344° C. and for a steady-state period of at least 3.5 hrs for each temperature condition. The resulting acrylic acid yield (Y), propionic acid concentration ([PA]), and carbon accountability were calculated as follows:

$$Y (\%) = 100 \times \left( \frac{\text{moles acrylic acid produced}}{\text{moles propane fed}} \right)$$

$$[PA](\text{ppm}) = 10^6 \times \frac{\text{mass propionic acid}}{\text{mass propionic acid} + \text{mass acrylic acid}}$$

$$\text{Carbon accountability}(\%) = 100 \times \frac{\sum \text{moles carbon out}^*}{3 \times \text{moles propane fed}}$$

*As quantified by gas chromatography analysis of the reactor effluent for the sum of all major carbonaceous species including propane, propylene, acrylic acid, acetic acid, propionic acid, carbon monoxide, and carbon dioxide.

The reactor effluent was analyzed by gas chromatography using an SRI Instruments Model 8610C Gas Chromatograph. The non-condensible gases including $O_2$, $N_2$, CO, $CO_2$, propane, and propylene were separated by series molecular sieve 5A (91.4 cm by 0.318 cm dia.) and silica gel (182.9 cm by 0.318 cm dia.) packed columns; detection of these gases was by thermal conductivity. The effluent liquids (e.g., acetic, propionic, and acrylic acids) were separated using a carbowax capillary column (30 m by 0.53 mm dia., 1.2 μm film) and detected by flame ionization.

The results are shown in Table 2.

TABLE 2

| | Comparative Example 1 Results | | | |
| --- | --- | --- | --- | --- |
| Furnace temp. (° C.) | Catalyst bed peak temp. (° C.) | Acrylic acid yield (%) | Propionic acid conc. (ppm) | Carbon accountability (%) |
| 310 | 321 | 23.9 | 23,730 | 103.2 |
| 320 | 335 | 32.3 | 12,420 | 102.6 |
| 330 | 350 | 41.0 | 6,365 | 101.4 |
| 337 | 360 | 46.2 | 3,965 | 100.4 |
| 342 | 372 | 51.5 | 2,648 | 101.5 |
| 344 | 375 | 52.4 | 2,481 | 101.0 |

Example 1

A bulk powder iron phosphate catalyst having a $FeP_{1.7}O_{5.8}$ bulk composition (as measured by X-ray fluorescence) was synthesized and pressed to particles of 14 to 20 mesh particles.

A two-stage catalyst bed was loaded into a stainless steel plug flow tubular reactor of the same design as described in Comparative Example 1. The first catalyst stage was a 4 cm long catalyst bed comprising 4.47 g of the MMO catalyst mixed with 4 cc of inert carborundum packing. The MMO sample used in this experiment, Example 1, was a fresh aliquot of the identical catalyst batch prepared for Comparative Example 1. The second catalyst stage comprised a neat, 1.7 g bed of the iron phosphate catalyst. The first stage catalyst bed was charged to the reactor tube such that it was also centered along the length of the reactor tube, and the second stage was placed immediately following the first stage, i.e., the two catalyst stages were in contact with each other. The remaining volume of the reactor tube was loaded with inert carborundum packing.

A vapor feed comprising 7.0% propane, 70.0% air, and 23% water was fed to the reactor at a total flow rate of 80 standard cubic centimeters per minute. The feed first contacted the first catalyst stage, which comprised the MMO catalyst and carborundum packing, and the products of the oxidation reaction exited the first stage and immediately entered the second catalyst stage, which comprised the neat iron phosphate catalyst.

The reaction was conducted at furnace temperatures ranging from 300 to 342° C. and for a steady-state period of at least 3.5 hrs for each temperature condition. The resulting acrylic acid yield on propane and the concentration of propionic acid on an acrylic acid basis were calculated as defined in Comparative Example 1. Example 1 results are shown in Table 3.

TABLE 3

Example 1 Results

| Furnace temp. (° C.) | Catalyst bed peak temp. (° C.) | Acrylic acid yield (%) | Propionic acid conc. (ppm) | Carbon accountability (%) |
|---|---|---|---|---|
| 310 | 316 | 17.2 | 19,687 | 100.9 |
| 320 | 329 | 25.5 | 9,760 | 99.0 |
| 330 | 348 | 45.1 | 3,621 | 101.3 |
| 337 | 371 | 52.6 | 2,103 | 97.9 |
| 342 | 380 | 52.9 | 2,115 | 100.7 |

Example 2

A bulk powder mixed metal oxide catalyst having a $CsMo_{12}PAsV_{0.2}Cu_{0.2}Sb_{0.1}$ oxide bulk composition was synthesized and pressed to particles of 14 to 20 mesh particle size.

This catalyst was used in place of the second catalyst stage in an experiment analogous to that presented in Example 1. A neat 2.4 g charge of the $CsMo_{12}PAsV_{0.2}Cu_{0.2}Sb_{0.1}$ oxide catalyst was used in this case.

The propane oxidation reaction was conducted identically to the procedure in Example 1. Example 2 results are shown in Table 4.

TABLE 4

Example 2 Results

| Furnace temp. (° C.) | Catalyst bed peak temp. (° C.) | Acrylic acid yield (%) | Propionic acid conc. (ppm) | Carbon accountability (%) |
|---|---|---|---|---|
| 310 | 325 | 23.6 | 14,842 | 99.7 |
| 320 | 344 | 31.6 | 5,232 | 99.2 |
| 323 | 345 | 33.4 | 4,695 | 99.4 |
| 327 | 347 | 37.8 | 3,251 | 98.6 |
| 330 | 354 | 42.3 | 2,579 | 97.7 |
| 337 | 359 | 47.8 | 1,878 | 99.8 |
| 342 | 371 | 49.4 | 1,640 | 99.9 |

Example 3

PA is removed from a product AA stream by an aldol condensation reaction with an aldehyde.

AA is obtained by the selective vapor phase oxidation of propane or propylene using catalysts known to those skilled in the art to yield an oxidation product gas containing acrylic, acetic, and propionic acids in addition to the typical constituents (e.g., water of oxidation and of feed steam, unconverted oxygen, nitrogen, carbon monoxide, carbon dioxide and side reaction products) of these selective partial oxidations.

The acids are isolated from the product gas by known separation techniques, such as absorption of the acids into water followed by extraction of the acids into a solvent or the direct absorption of the acids into a solvent. A substantially water-free product acid stream is then obtained by, in the case of a light solvent, distilling the solvent from the acid/solvent mixture or, in the case of a heavy solvent, distilling the acids from the acid/solvent mixture.

The resulting substantially water-free product acid stream is then vaporized and fed along with an aldehyde, such as formaldehyde, to an aldol condensation reactor. The aldol condensation reactor is designed to conduct catalytic, vapor phase aldol condensations as known to those skilled in the art. Suitable catalysts include oxides of sodium, potassium, cesium, and niobium supported on silica.

The acrylic acid fed to the aldol condensation reactor passes through the process unreacted, as expected, because the aldol condensation reaction occurs between species having saturated carbon-carbon bonds and an aldehyde to form unsaturated adducts. Thus, the saturated aliphatic acids are converted. When formaldehyde is the aldehyde, the acetic acid and PA are converted, respectively, to AA and methacrylic acid. AA formed from the acetic acid improves the process yield. Methacrylic acid formed from the propionic acid can be removed from the acrylic acid by distillation (as a bottoms product) or tolerated as an impurity (and a co-polymerizable one in the case of polymer end use).

Comparative Example 2

A stream of AA (NBP 141.6° C.) containing 5000 ppm of PA (NBP 141.1° C.), as well as several weight percent of lower boiling components (e.g. acetic acid; NBP 118.5° C.) and several weight percent of higher boiling components (e.g. acryloxypropionic acid) is fed to the lower portion of a simple distillation column packed with an inert material (e.g ceramic Raschig rings or saddles). The objective is to reduce the level of the PA about 10-fold by distilling it overhead with an equal amount of AA and the lower boiling materials and to recover the AA and the higher boiling materials as a bottoms product. Assuming a PA/AA relative volatility of about 1.01, the minimum packing height required to effect the separation is equivalent to about 800 theoretical stages, making the objective of AA separation unrealistic.

The normal boiling points listed above were taken from the CRC "Handbook of Chemistry and Physics". Other sources, DIPPR (Design Institute for Physical Property Data sponsored by the AIChE) for example, suggest a very small NBP difference between acrylic acid and propionic acid in just the opposite direction. This emphasizes the difficulty of the separation via simple distillation. For all practical purposes, in normal industrial AA purification columns, AA and PA co-distill.

Example 4

Amberlyst™ 15 resin of Rohm and Haas Company, a strongly acidic, macroreticular, ion exchange resin with sulfonic acid functionality (4.9 meq/g), is treated with an aqueous solution of silver nitrate to convert the resin from the acid form to the silver ion form. The converted resin is rinsed with water and dried in a vacuum oven.

A stream of acrylic acid, similar to that of Comparative Example 2, containing 5000 ppm of PA as well as several weight percent of lower boiling components (e.g. acetic acid) and several weight percent of higher boiling components (e.g. acryloxypropionic acid) is fed to the upper portion of a distillation column packed with the Ag-form Amberlyst 15. The packing height is equivalent to 100 theoretical stages of unfunctionalized resin. The column is operated with a reflux ratio of 1000 with the objective of reducing the PA level about 10-fold by distilling it overhead with an equal amount of AA and the lower boiling materials and recovering the acrylic acid and the higher boiling materials as a bottom products. The lower boiling materials and a substantial portion of the PA are taken overhead. AA, with a reduced propionic acid content is recovered as the bottoms stream.

Comparative Example 3

Vapor-liquid equilibrium data were obtained experimentally for the binary isobutyric acid (IBA) and methacrylic acid (MAA) system using methods known to those skilled in the art, such as described in *Vapor-Liquid Equilibrium Data Collection,* J. Gmehling et al., DECHEMA Chemistry Data Series, Vol. I, 40 parts, DECHEMA, Frankfurt, first volume 1977. From these data, the minimum number of theoretical distillation stages at total reflux was calculated from the Fenske Equation for a 2 mole % IBA in MMA feed, an overhead IBA stream containing 5 mole % MAA and a bottoms MAA stream containing less than 0.01 mole % IBA. The minimum number of theoretical stages was 47.

Example 5

Vapor-liquid equilibrium data were obtained experimentally for a three-component IBA, MAA and dimethyl sulfoxide (DMSO) system, wherein the ratio of DMSO to MAA was 2:1. From these data, the minimum number of theoretical distillation stages at total reflux was calculated using the same methodology as in Comparative Example 3, except that the IBA/MAA data were calculated on a DMSO-free basis. The minimum number of theoretical stages was 27.

What is claimed is:

1. A method for producing an unsaturated carboxylic acid product by the selective partial oxidation of an alkane comprising:
   i. reacting an alkane with oxygen or an oxygen-containing gas, in the presence of a catalyst to yield a product comprising at least one unsaturated carboxylic acid and a concentration of saturated carboxylic acid; and,
   ii. lowering the concentration of the saturated carboxylic acid by lowering the partial oxidation reaction selectivity to the saturated carboxylic acid, destroying, converting, or separating at least a portion of the saturated carboxylic acid;
   wherein the catalyst comprises:
      (a) a mixed metal oxide comprising the empirical formula $A_a M_b N_c X_d Z_e O_f$ wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and
         wherein, when $a=1$, $b=0.01$ to $1.0$, $c=0.01$ to $1.0$, $d=0.01$ to $1.0$, $e=0$ to $0.1$, and f is dependent on the oxidation state of the other elements; and,
      (b) an oxidative dehydrogenation catalyst.

2. The method of claim 1 wherein
   i. the alkane comprises propane; and
   ii. the unsaturated carboxylic acid comprises acrylic acid.

3. The method of claim 1 wherein the lowering of the saturated carboxylic acid concentration comprises adding a catalyst wherein the catalyst is at least one oxide of a metal selected from the group comprising Mo, P, Fe, and V or combinations thereof.

4. A method for producing an unsaturated carboxylic acid product by the selective partial oxidation of an alkane comprising:
   i. reacting an alkane with oxygen or an oxygen-containing gas, in the presence of a catalyst to yield a product comprising at least one unsaturated carboxylic acid and a concentration of saturated carboxylic acid; and,
   ii. lowering the saturated carboxylic acid concentration by operating an aldol condensation of the saturated carboxylic acid wherein the saturated carboxylic acid is reacted with an aldehyde;
   wherein the catalyst comprises:
   a mixed metal oxide comprising the empirical formula $A_a M_b N_c X_d Z_e O_f$ wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when $a=1$, $b=0.01$ to $1.0$, $c=0.01$ to $1.0$, $d=0.01$ to $1.0$, $e=0$ to $0.1$, and f is dependent on the oxidation state of the other elements.

5. A method for producing an unsaturated carboxylic acid product by the selective partial oxidation of an alkane comprising:
   i. reacting an alkane with oxygen or an oxygen-containing gas, in the presence of a catalyst to yield a product comprising at least one unsaturated carboxylic acid and a concentration of saturated carboxylic acid; and,
   ii. lowering the saturated carboxylic acid concentration by operating an adsorptive distillation or an extractive distillation process;
   wherein the catalyst comprises:
   a mixed metal oxide comprising the empirical formula $A_a M_b N_c X_d Z_e O_f$ wherein A is at least one element selected from the group consisting of Mo and W; M is at least one element selected from the group consisting of V and Ce; N is at least one element selected from the group consisting of Te, Sb and Se; X is at least one element selected from the group consisting of Nb, Ta, Ti, Al, Zr, Cr, Mn, Fe, Ru, Co, Rh, Ni, Pt, Sb, Bi, B, In, As, Ge, Sn, Li, Na, K, Rb, Cs, Fr, Be, Mg, Ca, Sr, Ba, Ra, Hf, Pb, P, Pm, Eu, Gd, Dy, Ho, Er, Tm, Yb and Lu; and Z is at least one element selected from the group consisting of Zn, Ga, Ir, Sm, Pd, Au, Ag, Cu, Sc, Y, Pr, Nd and Tb; and wherein, when $a=1$, $b=0.01$ to $1.0$, $c=0.01$ to $1.0$, $d=0.01$ to $1.0$, $e=0$ to $0.1$, and f is dependent on the oxidation state of the other elements.

6. The method of claim 5 wherein the operating an extractive distillation process comprises;
   i. a lewis base is complexed with acrylic acid; and,
   ii. the acrylic complexed with the lewis based is separated from propionic acid.

* * * * *